United States Patent
Srivastava et al.

(10) Patent No.: US 10,888,455 B2
(45) Date of Patent: Jan. 12, 2021

(54) IMAGE-GUIDED DELIVERY OF OPHTHALMIC THERAPEUTICS

(71) Applicant: THE CLEVELAND CLINIC FOUNDATION, Cleveland, OH (US)

(72) Inventors: Sunil K. Srivastava, Shaker Heights, OH (US); Justis P. Ehlers, Shaker Hts., OH (US); Yuankai K. Tao, Shaker Hts., OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 90 days.

(21) Appl. No.: 16/381,123

(22) Filed: Apr. 11, 2019

(65) Prior Publication Data

US 2019/0231591 A1    Aug. 1, 2019

Related U.S. Application Data

(62) Division of application No. 14/886,428, filed on Oct. 19, 2015, now Pat. No. 10,278,859.

(Continued)

(51) Int. Cl.
*A61M 31/00* (2006.01)
*A61F 9/00* (2006.01)
(Continued)

(52) U.S. Cl.
CPC ............ *A61F 9/0017* (2013.01); *A61B 3/102* (2013.01); *A61F 9/0026* (2013.01); *G16H 10/60* (2018.01)

(58) Field of Classification Search
CPC .......................... A61F 9/0008–9/0026; A61F 9/00736–9/00763; A61F 9/0017;
(Continued)

(56) References Cited

U.S. PATENT DOCUMENTS

| 3,074,407 A | 1/1963 | Moon et al. |
| 4,205,682 A | 6/1980 | Crock et al. |

(Continued)

FOREIGN PATENT DOCUMENTS

| DE | 10317367 A1 | 1/2004 |
| EP | 1081647 A1 | 3/2001 |

(Continued)

OTHER PUBLICATIONS

PCT International Search Report for corresponding PCT Application Serial No. PCT/US2015/056170, dated Jan. 22, 2016, pp. 1-11.

(Continued)

*Primary Examiner* — Jason E Flick
(74) *Attorney, Agent, or Firm* — Tarolli, Sundheim, Covell & Tummino LLP

(57) ABSTRACT

Systems and methods are provided for image-guided delivery of therapeutics to an eye. An optical coherence tomography (OCT) imager is configured to produce at least one OCT image of the eye. A therapeutic delivery system is configured to deliver a therapeutic to the eye through a distal end of a delivery mechanism. A system control is configured to determine a position of the distal end of the delivery mechanism and control the therapeutic delivery system according to at least the determined position.

14 Claims, 3 Drawing Sheets

Related U.S. Application Data

(60) Provisional application No. 62/065,444, filed on Oct. 17, 2014.

(51) Int. Cl.
  *G16H 10/60* (2018.01)
  *A61B 3/10* (2006.01)

(58) Field of Classification Search
  CPC ....... G06F 19/322; G16H 10/60; A61B 3/102; A61M 5/142–5/155; A61M 2205/33–2205/3396; A61M 5/172–2005/172
  See application file for complete search history.

(56) References Cited

U.S. PATENT DOCUMENTS

| | | | |
|---|---|---|---|
| 4,796,623 | A | 1/1989 | Krasner et al. |
| 5,288,292 | A | 2/1994 | Giraud et al. |
| 5,290,301 | A | 3/1994 | Lieberman |
| 6,613,061 | B1 | 9/2003 | Olson et al. |
| 2014/0206940 | A1* | 7/2014 | Hufford ................. A61B 1/06 600/158 |
| 2014/0221822 | A1 | 8/2014 | Ehlers et al. |

FOREIGN PATENT DOCUMENTS

| | | |
|---|---|---|
| WO | 89/00404 A1 | 1/1989 |
| WO | 03/30073 A1 | 4/2003 |
| WO | 2013/148687 A2 | 10/2013 |
| WO | 2013/151879 A1 | 10/2013 |
| WO | 2014/081875 A1 | 5/2014 |

OTHER PUBLICATIONS

Bahar, Irit, et al. "Comparison of three different techniques of corneal transplantation for keratoconus." American journal of ophthalmology 146.6 (2008): 905-912.
Campbell, John Peter, et al. "Wide-field retinal imaging in the management of noninfectious posterior uveitis." American journal of ophthalmology 154.5 (2012): 908-911.
Ehlers, Justis P., et al. "Contrast-enhanced intraoperative optical coherence tomography." British Journal of Ophthalmology 97.11 (2013): 1384-1386.
Fischer, M. Dominik, et al. "Successful subretinal delivery and monitoring of MicroBeads in mice." PloS one 8.1 (2013): e55173.
Fontana, Luigi, Gabriella Parente, and Giorgio Tassinari. "Clinical outcomes after deep anterior lamellar keratoplasty using the big-bubble technique in patients with keratoconus." American journal of ophthalmology 143.1 (2007): 117-124.
Freund, K. B. S. A. Shah, and V. P. Shah. "Correlation of transient vision loss with outer retinal disruption following intravitreal ocriplasmin." Eye 27.6 (2013): 773.
Hibi, Nobuaki, et al. "Relationship between retinal layer thickness and focal macular electroretinogram components after epiretinal membrane surgery." Investigative ophthalmology & visual science 54.12 (2013): 7207-7214.
Ehlers, Justis P., et al. "Intrasurgical dynamics of macular hole surgery: an assessment of surgery-induced ultrastructural alterations with intraoperative optical coherence tomography." Retina 34.2 (2014): 213-221.
Itoh, Yuji, et al. "Assessment of retinal alterations after intravitreal ocriplasmin with spectral-domain optical coherence tomography." Ophthalmology 121.12 (2014): 2506-2507.
Joos, Karen M., and Jin-Hui Shen. "Miniature real-time intraoperative forward-imaging optical coherence tomography probe." Biomedical optics express 4.8 (2013): 1342-1350.
Jung, Gila, et al. "Genetically modified neural stem cells for a local and sustained delivery of neuroprotective factors to the dystrophic mouse retina." Stem cells translational medicine 2.12 (2013): 1001-1010.
Kang, Dong-Goo, Dae Chul Suh, and Jong Beom Ra. "Three-dimensional blood vessel quantification via centerline deformation." IEEE Transactions on Medical Imaging 28.3 (2008): 405-414.
Kempen et al., "Flourescein angiography versus optical coherence tomography for diagnosis of uveitic maular edema." Ophthalmology 120.9 (2013): 1852-1859.
Klein, Thomas, et al. "Joint aperture detection for speckle reduction and increased collection efficiency in ophthalmic MHz OCT." Biomedical optics express 4.4 (2013): 619-634.
Melles, Gerrit RJ, et al. "A new surgical technique for deep stromal, anterior lamellar keratoplasty." British Journal of Ophthalmology 83.3 (1999): 327-333.
Meng, F., et al. "Induction of retinal ganglion-like cells from fibroblasts by adenoviral gene delivery." Neuroscience 250 (2013): 381-393.
Ehlers, Justis P., et al. "Novel microarchitectural dynamics in rhegmatogenous retinal detachments identified with intraoperative optical coherence tomography." Retina 33.7 (2013): 1428-1434.
Nassif, N. A., et al. "In vivo high-resolution video-rate spectral-domain optical coherence tomography of the human retina and optic nerve." Optics express 12.3 (2004): 367-376.
Nicholson, Benjamin P., et al. "Comparison of wide-field fluorescein angiography and 9-field montage angiography in uveitis." American journal of ophthalmology 157.3 (2014): 673-677.
Oberkampf, Denis, Daniel F. DeMenthon, and Larry S. Davis. "Iterative pose estimation using coplanar points." Proceedings of IEEE Conference on Computer Vision and Pattern Recognition. IEEE, 1993.
Pan, Carolyn K., et al. "Embryonic stem cells as a treatment for macular degeneration." Expert opinion on biological therapy 13.8 (2013): 1125-1133.
Ehlers, Justis P., et al. "Analysis of pars plana vitrectomy for optic pit-related maculopathy with intraoperative optical coherence tomography: a possible connection with the vitreous cavity." Archives of ophthalmology 129.11 (2011): 1483-1486.
Patel, Ravi D., et al. "Characterization of ischemic index using ultra-widefield fluorescein angiography in patients with focal and diffuse recalcitrant diabetic macular edema." American journal of ophthalmology 155.6 (2013): 1038-1044.
Patton, Niall, et al. "Retinal image analysis: concepts, applications and potential." Progress in retinal and eye research 25.1 (2006): 99-127.
Petersen, Thomas. "A comparison of 2d-3d pose estimation methods." Aalborg University-Institute for Media Technology Computer vision and graphics. Aalborg University (2008).
Ehlers, "Pioneer: a prospective intraoperative and perioperative oct study—6 month vitreoretinal results", Sunday, Aug. 26, 2012, 4:00PM, Imaging Symposium, ASRS 30th Annual Meeting, pp. 1-4.
Ehlers, Justis P., et al. "Factors associated with persistent subfoveal fluid and complete macular hole closure in the Pioneer study." Investigative ophthalmology & visual science 56.2 (2015): 1141-1146.
Ray, Robin, et al. "Intraoperative microscope-mounted spectral domain optical coherence tomography for evaluation of retinal anatomy during macular surgery." Ophthalmology 118.11 (2011): 2212-2217.
Reinhart, William J., et al. "Deep anterior lamellar keratoplasty as an alternative to penetrating keratoplasty: a report by the American Academy of Ophthalmology." Ophthalmology 118.1 (2011): 209-218.
Sim, Dawn A., et al. "Patterns of peripheral retinal and central macula ischemia in diabetic retinopathy as evaluated by ultra-widefield fluorescein angiography." American journal of ophthalmology 158.1 (2014): 144-153.
Singer, Michael, et al. "Area of peripheral retinal nonperfusion and treatment response in branch and central retinal vein occlusion." Retina 34.9 (2014): 1736-1742.
Song, Cheol, et al. "Fiber-optic OCT sensor guided "SMART" micro-forceps for microsurgery." Biomedical optics express 4.7 (2013): 1045-1050.

(56) References Cited

OTHER PUBLICATIONS

Ehlers, Justis P., et al. "Integration of a spectral domain optical coherence tomography system into a surgical microscope for intraoperative imaging." Investigative ophthalmology & visual science 52.6 (2011): 3153-3159.

Tao, Yuankai K., et al. "Intraoperative spectral domain optical coherence tomography for vitreoretinal surgery." Optics letters 35.20 (2010): 3315-3317.

Ehlers, Justis P., et al. "Visualisation of contrast-enhanced intraoperative optical coherence tomography with indocyanine green." British journal of ophthalmology 98.11 (2014): 1588-1591.

Ehlers, Justis P., et al. "Visualization of real-time intraoperative maneuvers with a microscope-mounted spectral domain optical coherence tomography system." Retina (Philadelphia, Pa.) 33.1 (2013): 232.

Wessel, Matthew M., et al. "Peripheral retinal ischaemia, as evaluated by ultra-widefield fluorescein angiography, is associated with diabetic macular oedema." British Journal of Ophthalmology 96.5 (2012): 694-698.

West, Jay B., and Calvin R. Maurer. "Designing optically tracked instruments for image-guided surgery." IEEE transactions on medical imaging 23.5 (2004): 533-545.

Wojtkowski, Maciej, et al. "Ultrahigh-resolution, high-speed, Fourier domain optical coherence tomography and methods for dispersion compensation." Optics express 12.11 (2004): 2404-2422.

Xu, David, et al. "Automated volumetric analysis of interface fluid in descemet stripping automated endothelial keratoplasty using intraoperative optical coherence tomography." Investigative ophthalmology & visual science 55.9 (2014): 5610-5615.

Xu, David, et al. "A novel segmentation algorithm for volumetric analysis of macular hole boundaries identified with optical coherence tomography." Investigative ophthalmology & visual science 54.1 (2013): 163-169.

Zhang, Zhengyou. "A flexible new technique for camera calibration." IEEE Transactions on pattern analysis and machine intelligence 22 (2000).

\* cited by examiner

IMAGE-GUIDED DELIVERY OF OPHTHALMIC THERAPEUTICS

RELATED APPLICATIONS

This application is a divisional of U.S. patent application Ser. No. 14/886,428, filed 19 Oct. 2015, which claims priority from U.S. Patent Application Ser. No. 62/065,444, filed 17 Oct. 2014, each of which is incorporated herein by reference in its entirety.

GOVERNMENT INTEREST

This invention was made with government support under EY022947 awarded by the National Institutes of Health. The government has certain rights in the invention.

TECHNICAL FIELD

This invention relates to medical systems, and more particularly, to image-guided delivery of ophthalmic therapeutics.

BACKGROUND

Novel therapeutics in ophthalmology are currently going through a massive expansion in disease applications and mechanisms. Numerous diseases ranging from inherited retinal degenerations to acquired diseases, such as macular degeneration, are potentially amenable to many of these therapeutics, including stem cell delivery, gene therapy, small molecule pharmacotherapy, and other biologics. Many of these therapies are highly dependent on precision delivery to the area of interest.

SUMMARY OF THE INVENTION

In accordance with an aspect of the present invention, a system is provided for image-guided delivery of therapeutics to an eye. An optical coherence tomography (OCT) imager is configured to produce at least one OCT image of the eye. A therapeutic delivery system is configured to deliver a therapeutic to the eye through a distal end of a delivery mechanism. A system control is configured to determine a position of the distal end of the delivery mechanism and control the therapeutic delivery system according to at least the determined position.

In accordance with another aspect of the present invention, a method is provided for image-guided delivery of a therapeutic to an eye. At least one optical coherence tomography (OCT) image of the eye is generated. A position of a distal end of a therapeutic delivery mechanism is determined from the at least one OCT image of the eye. The therapeutic is delivered to the eye through the therapeutic delivery mechanism according to the determined position of the distal end of the therapeutic delivery mechanism. The delivery of the therapeutic is monitored from the at least one OCT image. The therapeutic delivery system is controlled according to the monitored delivery of the therapeutic.

In accordance with yet another aspect of the present invention, a system is provided for automated delivery of therapeutics to an eye. An optical coherence tomography (OCT) imager is configured to produce at least one OCT image of the eye. A therapeutic delivery system is configured to deliver a therapeutic to the eye through a distal end of a delivery mechanism. A system control is configured to monitor the delivery of the therapeutic from the at least one OCT image and control the therapeutic delivery system according to at least one of a determined flow velocity of the therapeutic, a determined delivered volume of the therapeutic, a determined leakage of the therapeutic from the delivery site, and a determined stress on tissue at the delivery site, and a determined strain on tissue at the delivery site.

DETAILED DESCRIPTION

In accordance with an aspect of the present invention, methods and systems are provided for image-guided and targeted delivery of ophthalmic therapeutics utilizing a microscope integrated OCT system, a surgeon or clinician can target these therapeutics to the area of interest. The resolution of the OCT allows for visualization both the target area as well as the instrument delivery system. The integrated OCT system provides immediate feedback of the cross-sectional location of the delivery system. Additionally, the volumetric nature of the integrated platform system allows for accurate measurement of the volume of the delivered therapeutic agent. Using a comprehensive image-guided OCT surgeon feedback system, expansion of the surgical manipulation is possible, including vibration dampened instruments, robotic assistance or guidance based on the image-guided feedback system.

Figure 1:
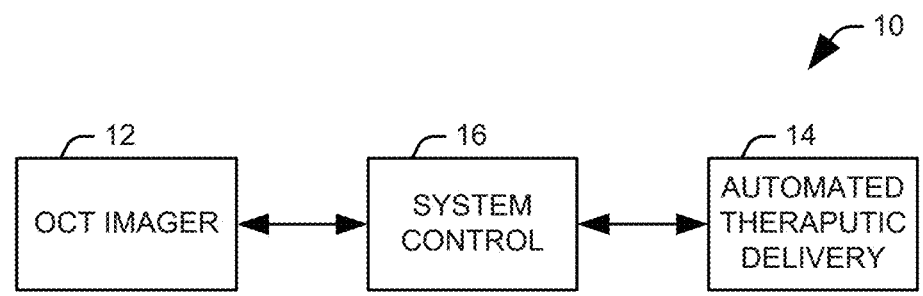
FIG. 1 illustrates one example of system for image-guided delivery of therapeutics to an eye.

FIG. 1 illustrates one example of system 10 for image-guided delivery of therapeutics to an eye. It will be appreciated that the system 10 can be configured to assist a user in manually performing a delivery of therapeutics to the eye or to partially or completely automate the delivery of therapeutics. It will be appreciated that the delivered therapeutic can include stem cells, nucleic acid polymers, pharmaceuticals, and other biologics.

The system 10 includes an optical coherence tomography (OCT) imager 12 configured to produce at least one OCT image of the eye. The OCT scanner 12 can be include any appropriate arrangement for providing OCT images, such as time domain OCT, swept source OCT, spatially encoded frequency OCT, and Doppler OCT. The system 10 further includes a therapeutic delivery system 14 configured to deliver the therapeutic to the eye through a distal end of a delivery mechanism. In one implementation, the therapeutic delivery system 14 includes a syringe with an injection tip that can be inserted into the eye and a pump to deliver the therapeutic at the injection site. As discussed previously, the therapeutic delivery system 14, in some implementations, will further include actuators for automatically inserting and withdrawing the injection tip into the eye.

A system control 16 is configured to determine a position of the distal end of the delivery mechanism and control the therapeutic delivery system 14 according to at least the determined position. It will be appreciated that the system control 16 can be implemented as a stand-alone unit operatively connected to each of the OCT scanner 12 and the therapeutic delivery system 14, or as part of either of the OCT scanner or the therapeutic delivery system 14. The system control 14 can be implemented as dedicated hardware, software instructions executed by an associated processor, or a combination of software and dedicated hardware. In one implementation, the position of the instrument tip can be tracked, with the system control 14 instructing haptic, audible, or visual feedback provided to the user when a desired location, such as a retinal layer of interest, is reached. Feedback can also be provided to stop the therapeutic delivery when a desired volume has been delivered.

In another implementation, real-time automated tissue segmentation algorithms can be applied to intraoperative OCT cross-sectional B-scan or volumetric datasets to guide automated drug delivery. It will be appreciated that this implementation, although referred to herein as "fully automated," does not preclude supervision and correction of the delivery process by a human operator. To this end, the position of instrument tips may be identified using en face OCT shadowing, cross-sectional contrast, or instrument-tracked imaging methods to locate specific treatment positions, and specific tissue layers targeted for therapeutic delivery may be identified before or during surgery and used as real-time triggers to control the therapeutic delivery system. To this end, a subretinal tissue layer of interest is targeted and injection automatically begins as the tip of the needle arrives at the layer-of-interest on OCT B-scans. If the instrument tip moves out of the subretinal space as a result of global motion or tremor, injection automatically stops. Finally, real-time volumetric segmentation can be used to precisely quantify the injected volume and stop or withdraw therapeutics as required.

Figure 2:
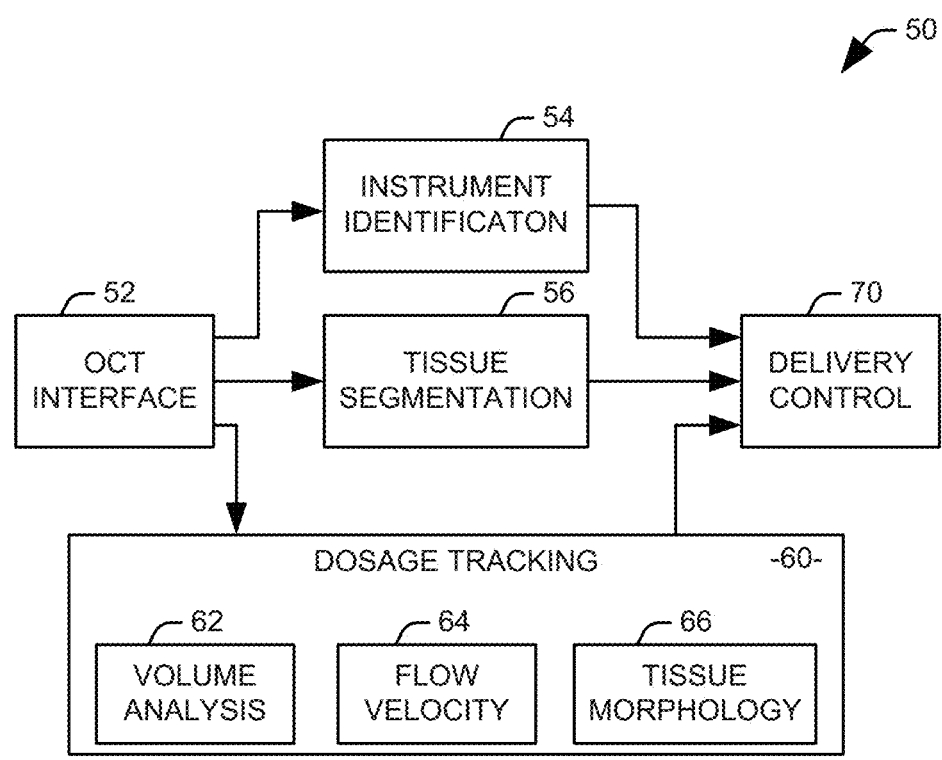
FIG. 2 illustrates one example of a system control in accordance with an aspect of the present invention.

FIG. 2 illustrates one example of a system control 50 in accordance with an aspect of the present invention. In the illustrated implementation, the system control 50 is implemented as software instructions executed by an associated processor in a stand-alone general purpose computer, although it will be appreciated that other configurations are possible. It will further be appreciated that the illustrated system control 50 is intended for a fully automated implementation, although the functional modules can operate similarly for a less-automated system.

The system control 50 includes an optical coherence tomography (OCT) interface 52 configured to receive at least one OCT image of the eye from an OCT system (not shown) and format the at least one OCT image for analysis by the system control 50. It will be appreciated that the OCT images can be provided in any form suitable for analysis, with examples including volumetric images and B-scans. Further, the OCT interface 52 can include digital filters and other components for conditioning the images for analysis as well as instructions for returning instructions to the OCT system. In one implementation, the OCT interface 52 can instruct the scanner to use specific scanning protocols to sparsely image the injection site for rapid measurements of injection volume in real-time, including variation of radial scans.

The received images are provided to each of an instrument identification component 54, a tissue segmentation component 56, and a dosage tracking component 60. The instrument identification component 54 is configured to determine a position of the distal end of the delivery mechanism within the at least one OCT image. For example, the instrument identification component 54 can utilized en face iOCT shadowing, cross-sectional contrast, or any other appropriate instrument tracking method. The tissue segmentation component 56 can be configured to determine a set of boundaries for tissue layers within the eye. In one implementation, the tissue layers are sub-surface retinal sublayers. It will be appreciated that these boundaries can be used to determine an appropriate delivery depth for the therapeutic. For example, the system control 50 can to instruct the therapeutic delivery system to deliver the therapeutic when it is determined that the tracked distal end is within a desired tissue layer.

The dosage tracking component 60 is configured to monitor the delivery of the therapeutic from the at least one OCT image. The dosage tracking component 60 includes a volume analysis component 62 configured to identify the delivered therapeutic within the at least one OCT image and determine a delivered volume from the identified therapeutic. For example, the volume analysis component 62 can include an edge recognition algorithm that determines a spatial extent of the delivered therapeutic within the image and calculates a volume from the spatial extent of the therapeutic. The volume analysis component 62 can further be configured to measure leakage of the delivered therapeutic from a site of delivery, allowing for a net delivery of the therapeutic to the delivery site to be calculated.

A flow velocity component 64 is configured to determine a flow velocity of the therapeutic from the at least one OCT image and determine an injection speed for the therapeutic. For example, the flow velocity component 64 can utilize any of Doppler OCT speckle variance, phase variance, or appropriate blood flow imaging techniques to acquire flow velocity measurements in real-time on cross-sectional B-scans at the injection site to calculate a therapeutic injection speed. A tissue morphology component 66 configured to measure one of stress and strain on tissue layers of interest. Specifically, changes in the tissue morphology can be monitored intraoperatively via real-time measurements of stress-strain on tissue layers-of-interest and used as real-time biomechanical feedback on acceptable rates of drug delivery.

The outputs of the instrument identification component 54, the tissue segmentation component 56, and the dosage tracking component 60 can be provided to a delivery control component 70 configured to provide an interface with the therapeutic delivery system allowing for control of the delivery system according to these outputs. For example, the delivery control component 70 can be configured to stop delivery of the therapeutic when the dosage tracking component 60 indicates that a desired dosage is achieved or if a measured stress or strain exceeds a predetermined threshold value. Alternatively, the delivery control 70 can select a delivery speed of the therapeutic according to the measured one of stress and strain.

The systems of FIGS. 1 and 2 significantly advance the field of targeted delivery of gene therapy, stem cells and regenerative medicine, and other biologics in the field of ophthalmology, particularly in the treatment of retinal diseases and degenerations. No current technologies exist for quantitating and confirming delivery of these therapeutics while confirming optimal location. Using live imaging of instrument/tissue interactions during surgical maneuvers in the eye. The high lateral and axial resolution of intraoperative OCT, down to several microns, allows for precision delivery of therapeutics to specific layers of interest intraoperatively. Effectively, automated therapeutic delivery can be performed by using OCT-guided feedback, including a position or depth of injection site and a volume of therapeutic delivered, to control a programmable syringe pump or similar device.

Figure 3:
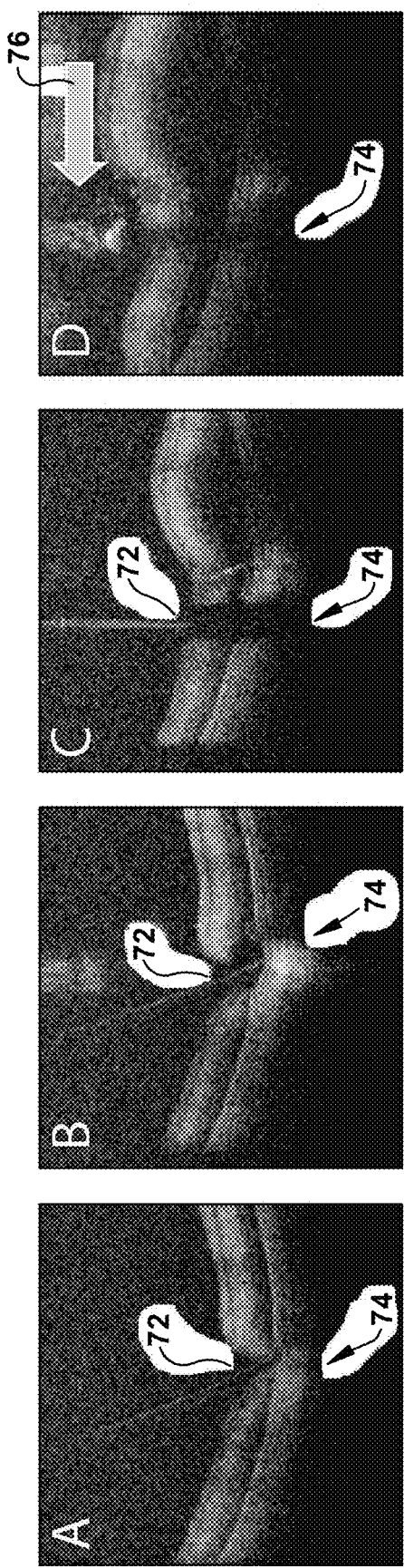
FIGS. 3A-3D illustrate an example a subretinal cannulation and injection in a porcine eye.

FIGS. 3A-3D illustrate an example 70 a subretinal cannulation and injection in a porcine eye. Each of FIGS. 3A-3D is a cross-sectional image of a subretinal region of the eye. FIG. 3A shows a needle tip 72 entering the subretinal space 74. FIG. 3B shows an initial injection volume displacing tissue surrounding the injection site. FIG. 3C illustrates the injection of the therapeutic into the subretinal space, with an accompanying elevation of the retina. In FIG. 3D, excess fluid and triamcinolone 76 is observed leaking from the injection site.

Figure 4:
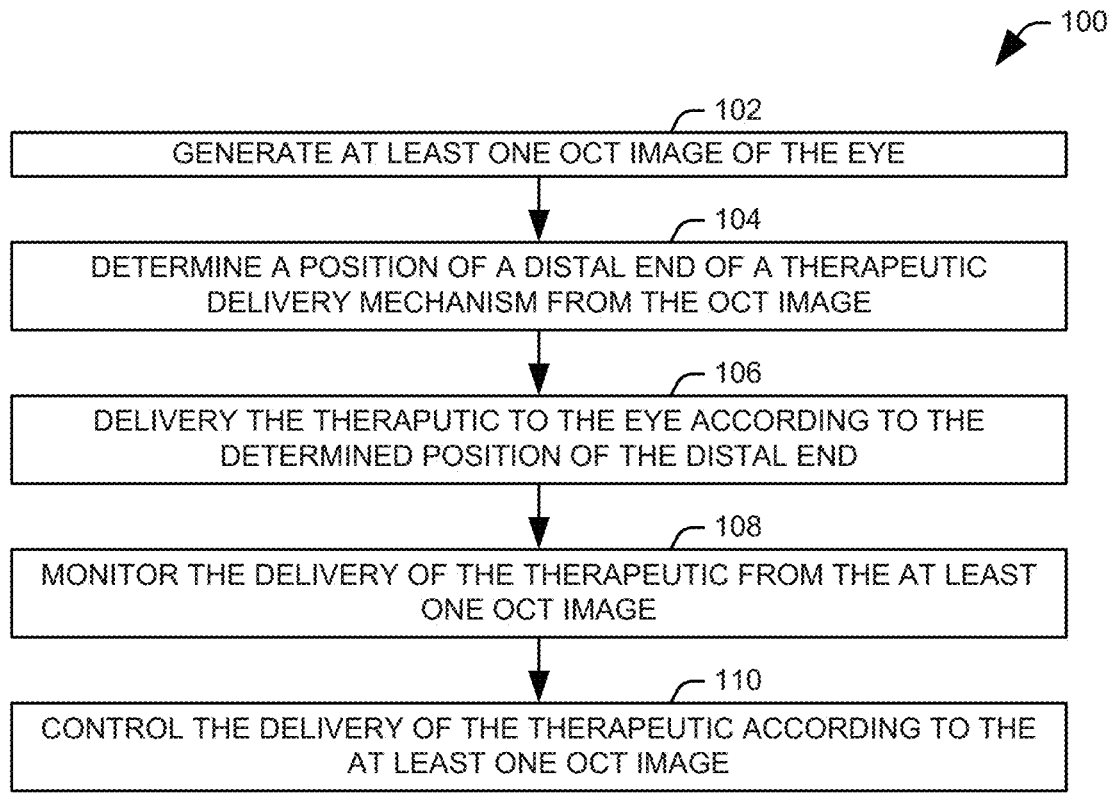
FIG. 4 illustrates a method for image-guided delivery of a therapeutic to an eye.

In view of the foregoing structural and functional features described above in FIGS. 1-3, an example method will be better appreciated with reference to FIG. 4. While, for purposes of simplicity of explanation, the method of FIG. 4 is shown and described as executing serially, it is to be understood and appreciated that the present invention is not limited by the illustrated order, as some actions could in other examples occur in different orders and/or concurrently from that shown and described herein.

FIG. 4 illustrates a method 100 for image-guided delivery of a therapeutic to an eye. At 102, at least one optical coherence tomography (OCT) image of the eye is generated. A position of a distal end of a therapeutic delivery mechanism is determined from the at least one OCT image of the eye at 104. In one example, this is done via en face OCT shadowing, although it will be appreciated that other methods for locating the distal end can be utilized. In one implementation, a set of boundaries are determined for tissue layers within the eye, with the position of the distal end determined relative to the tissue layer boundaries.

The therapeutic is delivered to the eye through the therapeutic delivery mechanism according to the determined position of the distal end of the therapeutic delivery mechanism at 106. For example, a syringe pump associated with the delivery mechanism can be activated when a desired delivery location is reached. For example, the therapeutic delivery system can be instructed to deliver the therapeutic when the distal end is within a desired tissue layer. Alternatively, the therapeutic delivery system can be instructed to provide one of haptic, audible, or visible feedback to the user to instruct the user to begin delivering the therapeutic.

At 108, delivery of the therapeutic is monitored from the at least one OCT image. It will be appreciated that at least one OCT image can include a time series of images, such that the delivery can be monitored over a period of time. In one implementation, an amount of therapeutic delivered to the eye can be tracked to determine a total dosage. This tracked volume can be refined by measuring leakage of the delivered therapeutic from the delivery site, such that a net delivered dosage can be calculated. Alternatively or additionally, a flow velocity of the delivered therapeutic can be measured. This can be used to compute or confirm a volume of delivered material or simply monitored to ensure that the flow velocity does not become sufficient to damage the tissue at the delivery site. A stress or strain on the tissue at the delivery site can also be monitored to determine an appropriate delivery velocity and to ensure that the tissue is not damaged during delivery of the therapeutic.

At 110, the therapeutic delivery system is controlled according to the at least one OCT image. Specifically, the observations from the monitoring at 108 can be applied to alter the manner in which the therapeutic is delivered to the patient. In one implementation, this can include stopping delivery of the therapeutic when a desired dosage is achieved. In another implementation, this can include adjusting a delivery speed, such as a flow velocity, according to a detected stress or strain on the tissue.

Figure 5:
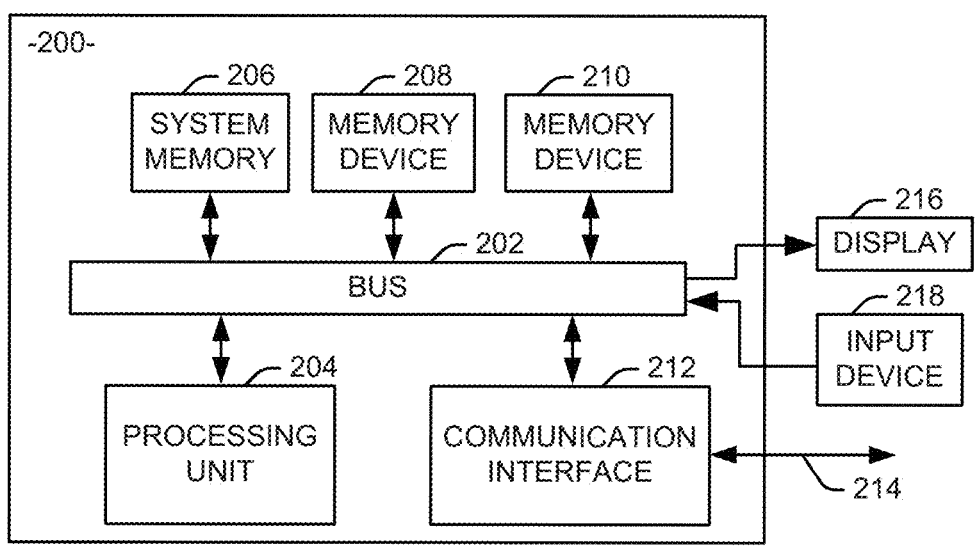
FIG. 5 is a schematic block diagram illustrating an exemplary system of hardware components capable of implementing examples of the systems and methods

FIG. 5 is a schematic block diagram illustrating an exemplary system 200 of hardware components capable of implementing examples of the systems and methods disclosed in FIGS. 1-4, such as the system control 16 illustrated in FIG. 1. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a therapeutic delivery system in accordance with the present invention. Computer executable logic for implementing the diagnostic system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can, in practice, refer to multiple, operatively connected apparatuses for storing machine executable instructions.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A method for image-guided delivery of a therapeutic to an eye comprising:
   generating at least one optical coherence tomography (OCT) image of the eye;
   determining a position of a distal end of a therapeutic delivery mechanism from the at least one OCT image of the eye;
   delivering the therapeutic to the eye through the therapeutic delivery mechanism according to the determined position of the distal end of the therapeutic delivery mechanism;
   monitoring the delivery of the therapeutic from the at least one OCT image; and
   controlling the therapeutic delivery system according to the at least one OCT image.

2. The method of claim 1, wherein monitoring the delivery of the therapeutic from the at least one OCT image comprises determining an amount of the therapeutic delivered to the eye, and controlling the therapeutic delivery system comprises stopping delivery of the therapeutic when a desired dosage is achieved.

3. The method of claim 2, wherein monitoring the delivery of the therapeutic from the at least one OCT image further comprises measuring leakage of the delivered therapeutic from a site of delivery.

4. The method of claim 1, wherein monitoring the delivery of the therapeutic from the at least one OCT image comprises measuring one of stress and strain on tissue layers of interest.

5. The method of claim 4, wherein controlling the therapeutic delivery system comprises determining a delivery speed for the therapeutic delivery system from the measured one of stress and strain.

6. The method of claim 1, wherein monitoring the delivery of the therapeutic from the at least one OCT image comprises measuring a flow velocity of the delivered therapeutic.

7. The method of claim 1, wherein determining a position of a distal end of a therapeutic delivery mechanism from the at least one OCT image of the eye comprises determining a set of boundaries for tissue layers within the eye, and delivering the therapeutic to the eye through the therapeutic delivery mechanism according to the determined position of the distal end of the therapeutic delivery mechanism comprises instructing the therapeutic delivery system to deliver the therapeutic when the distal end is within a desired tissue layer.

8. A method for image-guided delivery of a therapeutic to an eye comprising:
   generating at least one optical coherence tomography (OCT) image of the eye;
   determining a position of a distal end of a therapeutic delivery mechanism from the at least one OCT image of the eye;
   delivering the therapeutic to the eye through the therapeutic delivery mechanism according to the determined position of the distal end of the therapeutic delivery mechanism;
   monitoring the delivery of the therapeutic to a target area representing a biological area of interest from the at least one OCT image; and
   controlling the therapeutic delivery system according to the monitored delivery.

9. The method of claim 8, wherein monitoring the delivery of the therapeutic from the at least one OCT image comprises determining an amount of the therapeutic delivered to the eye, and controlling the therapeutic delivery system comprises stopping delivery of the therapeutic when a desired dosage is achieved.

10. The method of claim 9, wherein monitoring the delivery of the therapeutic from the at least one OCT image further comprises measuring leakage of the delivered therapeutic from a site of delivery.

11. The method of claim 8, wherein monitoring the delivery of the therapeutic from the at least one OCT image comprises measuring one of stress and strain on tissue layers of interest.

12. The method of claim 11, wherein controlling the therapeutic delivery system comprises determining a delivery speed for the therapeutic delivery system from the measured one of stress and strain.

13. The method of claim 8, wherein monitoring the delivery of the therapeutic from the at least one OCT image comprises measuring a flow velocity of the delivered therapeutic.

14. The method of claim 8, wherein determining a position of a distal end of a therapeutic delivery mechanism from the at least one OCT image of the eye comprises determining a set of boundaries for tissue layers within the eye, and delivering the therapeutic to the eye through the therapeutic delivery mechanism according to the determined position of the distal end of the therapeutic delivery mechanism comprises instructing the therapeutic delivery system to deliver the therapeutic when the distal end is within a desired tissue layer.

* * * * *